(12) United States Patent
Min et al.

(10) Patent No.: US 6,558,949 B2
(45) Date of Patent: May 6, 2003

(54) MEDIA FOR CULTURING HUMAN CELLS COMPRISING HUMAN SERUM AND METHOD FOR CULTURING HUMAN CELLS USING THE SAME

(76) Inventors: Byoung-Hyun Min, 204-401, Kummaeul Woosung Apt. Guin-dong, Dongan-ku, Anyang-shi, Kyoungi-do (KR); So Ra Park, 204-401, Kummaeul Woosung Apt. Guin-dong, Dongan-ku, Anyang-shi, Kyoungi-do (KR)

( * ) Notice: Subject to any disclaimer, the term of this patent is extended or adjusted under 35 U.S.C. 154(b) by 0 days.

(21) Appl. No.: 09/736,537

(22) Filed: Dec. 13, 2000

(65) Prior Publication Data

US 2001/0005590 A1 Jun. 28, 2001

(30) Foreign Application Priority Data

Dec. 14, 1999 (KR) ........................... 1999-57525

(51) Int. Cl.$^7$ ............... C12N 5/08; C12N 5/00; A01N 1/02; A61K 35/14; A61K 35/32
(52) U.S. Cl. ............ 435/366; 435/2; 435/392; 435/386; 435/240.2; 435/240.3; 435/240.23; 424/529; 424/531; 424/572; 424/574
(58) Field of Search .................. 424/529, 531, 424/572, 574; 435/2, 366, 240.2, 240.3, 240.23, 392, 386

(56) References Cited

U.S. PATENT DOCUMENTS

| 5,443,984 A | 8/1995 | Sawyer et al. |
|---|---|---|
| 5,858,783 A | 1/1999 | Goodwin et al. |
| 5,902,741 A | 5/1999 | Purchio et al. |
| 6,150,163 A | * 11/2000 | McPherson et al. ........ 435/384 |

OTHER PUBLICATIONS

Hay et al., ATCC Cell Lines and Hybridomas, 1994. American Type Culture Colllection, 8th, 521–522.*

* cited by examiner

Primary Examiner—Jon P. Weber
Assistant Examiner—Kailash C. Srivastava
(74) Attorney, Agent, or Firm—Merchant & Gould P.C.

(57) ABSTRACT

This invention relates to media for culturing human cells that the proliferation speed of human cells is increased and the cell expression type is stably manifested, and to a method for culturing human cells using the same. This invention is characterized in that the media used for culturing human cells comprises human serum.

6 Claims, 3 Drawing Sheets

1　2　3　4　5　　3-dimensional culture (wk)　1　2　3　4　5　　3-dimensional culture 1　2　3　4　　3-dimensional culture (wk)　1　2　3　4　　3-dimensional culture

MEDIA FOR CULTURING HUMAN CELLS COMPRISING HUMAN SERUM AND METHOD FOR CULTURING HUMAN CELLS USING THE SAME

FIELD OF THE INVENTION

The present invention relates to media for culturing human cells comprising human serum and a method for culturing human cells using the same.

BACKGROUND OF THE INVENTION

Typically, since it is difficult to regenerate cartilages, it is thus very difficult to treat diseases which occur therein such as arthritis.

To treat such a disease, a method was developed for culturing and proliferating patient's own chondrocytes in vitro, and grafting them to a diseased part thereafter. To accomplish such self-grafting, chondrocytes as many as possible are required and the peculiar expression-types of chondrocytes such as second-type collagen proteoglycan, etc. must also be maintained.

A present laboratory method for culturing chondrocytes used chiefly for cell grafting is to perform monolayered-culture of chondrocytes in appropriate media, then to proliferate them, to three-dimensionally culture them in alginate beads and to reconstruct the peculiar expression-types of the chondrocytes thereafter.

Since proliferation speed of chondrocytes, however, is very slow, long time is consumed to obtain a proper number of chondrocytes even though they are monolayer-cultured. In this process chondrocytes are dedifferentiated and three-dimensional culture is applied to reconstruct the expression types of the chondrocytes. But the problem is that the number of chondrocytes does not increase in this process.

DETAILED DESCRIPTION OF THE INVENTION

It is an object of the invention to provide media that can be used for culturing human cells including chondrocytes without generating conventional problems such as proliferation speed delay and loss of an expression types.

It is also another object of the invention to provide a method for culturing human cells using the aforementioned media.

The present invention is characterized in that the media used for culturing human cells comprise human serum, wherein the method comprises culturing human cells in the aforementioned media.

In a preferred embodiment, the media used for culturing the human cells comprise human serum of 1 to 50%(v/v).

In a preferred embodiment, the human, serum comprised in the media is originated from the blood of AB-type.

In a preferred embodiment, human cells cultured in the media are chondrocytes.

In a preferred embodiment, the media used for culturing the human cells comprise at least one selected from the group of including insulin, transferrin, selenium. T3 hormone and a mixture thereof.

In a preferred embodiment of the invention, the media used for culturing the human cells comprise at least one selected from the group of including a transforming growth factor (TGF-β), an insulin-like growth factor (IGF), a fibroblast growth factor (FGF), a platelet-derived growth factor (PDGF), a keratinocyte growth factor (KGF), an epidermic growth factor (EGF) and a mixture thereof.

In a preferred embodiment, for the media comprising the human serum and a method for culturing human cells cultured in the media, the serum comprised in the media and the cells cultured therein are originated from the same person.

The media for culturing human cells comprising human serum and a method for culturing human cells using the same in accordance with this invention are described in detail hereinafter.

It is preferred to derive the human serum used particularly in this invention from the blood of a patient who has given the cultured cells, but it may be obtained from a blood bank, and so on. Human serum from all blood types of O, A, B and AB can be used, but that from AB-type is preferred in particular. Human serum increases the proliferation speed of human cells and allows their expression type stably manifested. The amount of human serum of 1 to 50% (v/v), preferably 5 to 20% (v/v), may be added and used in the media for culturing human cells.

For the media for culturing human cells in which human serum may be added, all types of media generally used may be used. Examples of representative media include DMEM (Gibco BRL), Han's F-12 media (Gibco BRL), and so on.

Also, the media of this invention may further comprise at least one selected from the group including human-insulin, human-transferrin, sodium selenite, T3 hormone (3,3,5-triiodo-L-thryonine) and a mixture thereof. The amount of human-insulin and transferrin may be 1 mg/l through 15 mg/l respectively, and that of sodium selenite and T3 hormone may be 1 μg/l through 15 mg/l respectively. The media may further comprise a transforming growth factor-β (TGF-β), an insulin-like growth factor (IGF) a fibroblast growth factor (FGF), a platelet-derived growth factor (PDGF), a keratinocyte growth factor (KGF), a epidermal growth factor (EGF) and a mixture thereof. And the used amount thereof may be 1 μg/l through 10 μg/l.

Human cells that may be cultured in the media may be chondrocytes, liver cells, bone cells, nerve cells, myoblasts, and so on, but chondrocytes are most preferred. Human cells may be obtained from the cells separated by processing human tissues with appropriate ferments. For example, chondrocytes are obtained from the cells separated by processing chondrocyte tissues on both ends of a bone with hyaluronidase, trypsin, collagenase, etc. In particular, it is preferred to use human cells which are the patient's own cells who needs cell grafting.

Culturing of human cells may be performed according to any one of the known typical methods. A representative example is to perform primary cultivation of the chondrocytes for 5 to 28 days at the temperature of 35 to 39° C. with aeration of carbon dioxide of 5 to 15% in the media, and then three-dimensional cultivation of the chondrocytes, dedifferentiated in the process, for 3 to 14 days at 35 to 39° C. under carbon dioxide of 5 to 15% after inserting them into alginate beads.

The advantages of the method in accordance with the invention are that the culturing period can be shortened and the expression types of the cultivated cells can be stably manifested. The human cells obtained by the method in accordance with the invention may be used advantageously for cell or tissue grafting and has no considerable side effects along with the grafting.

DETAILED DESCRIPTION OF PREFERRED EMBODIMENTS

Embodiments in accordance with the invention are described hereinafter. The following embodiments are oily for illustrating the invention, and the scope of the invention is not limited to them.

A percentage (%) used in this description shows weight/weight percent (%) for solid/solid, weight/volume percent (%) for solid/liquid, and volume/volume percent (%) for liquid/liquid.

EMBODIMENT 1

Separated chondrocytes were obtained from chondrocyte tissues removed in nearthrosis substitution of a patient suffering from osteoarthritis, by processing in turn the tissues for one hour in hyaluronidase solution, then for one hour in trypsin solution of 0.2%, subsequently for 3 hours in collagenase solution of 0.2%.

These chondrocytes were primarily cultivated for about 4 weeks at 37° C. with aeration of air of 95% and carbon dioxide of 5% in the DMEM (acquired from Gibco BRL) comprising human serum of 10% (acquired from a blood bank). For the chondrocytes dedifferentiated by the primary culturing, three-dimensional culturing in the DMEM comprising the alginate beads of 2.0% (from Sigma) was applied for 1 week at 37° C. with aeration of air of 95% and carbon dioxide of 5%.

EMBODIMENT 2

The chondrocytes were cultivated with the same method as in the first embodiment, except that the DMEM comprising human serum of 10% and TGF-β of 5 ng/ml is used.

TEST EXAMPLE 1

Proliferation rate of chondrocytes depending on human serum concentration

The shapes of chondrocytes were examined by observing the chondrocyte media solution of the first and second embodiments under a backlight microscope. The number of chondrocytes was measured under the backlight microscope after staining the chondrocyte media with a trypanblue reagent according to the method described in the document {Acta Orthop Scand., 70(1), 55–61, (1999)}. And the proliferation rate was examined by measuring the amount of radioactivity in the chondrocytes after cultivating them in the media comprising [3H]-timidine according to the method described in the document {J. of Orthopadic Res., 15, 483–490(1997); Biochemica et Biophysica Acta, 1425, 505–515(1998)}.

Then, the media comprising fetal calf serum of 10% (fetal calf serum control group) and the media comprising fetal calf serum of 10% and 5 ng/ml, TGF-β (fetal calf serum/TGEF-β control group) were used as control groups. And the media for a common test group did not comprise serum. After culturing chondrocytes with the same method for the first embodiment, the shapes and proliferation rate of the chondrocytes were examined.

As the result the chondrocytes cultured according to the first and second embodiments showed the tendency gathering and lumping together, compared with the control groups, and the tendency was more intensified in subculturing.

Figure 1:
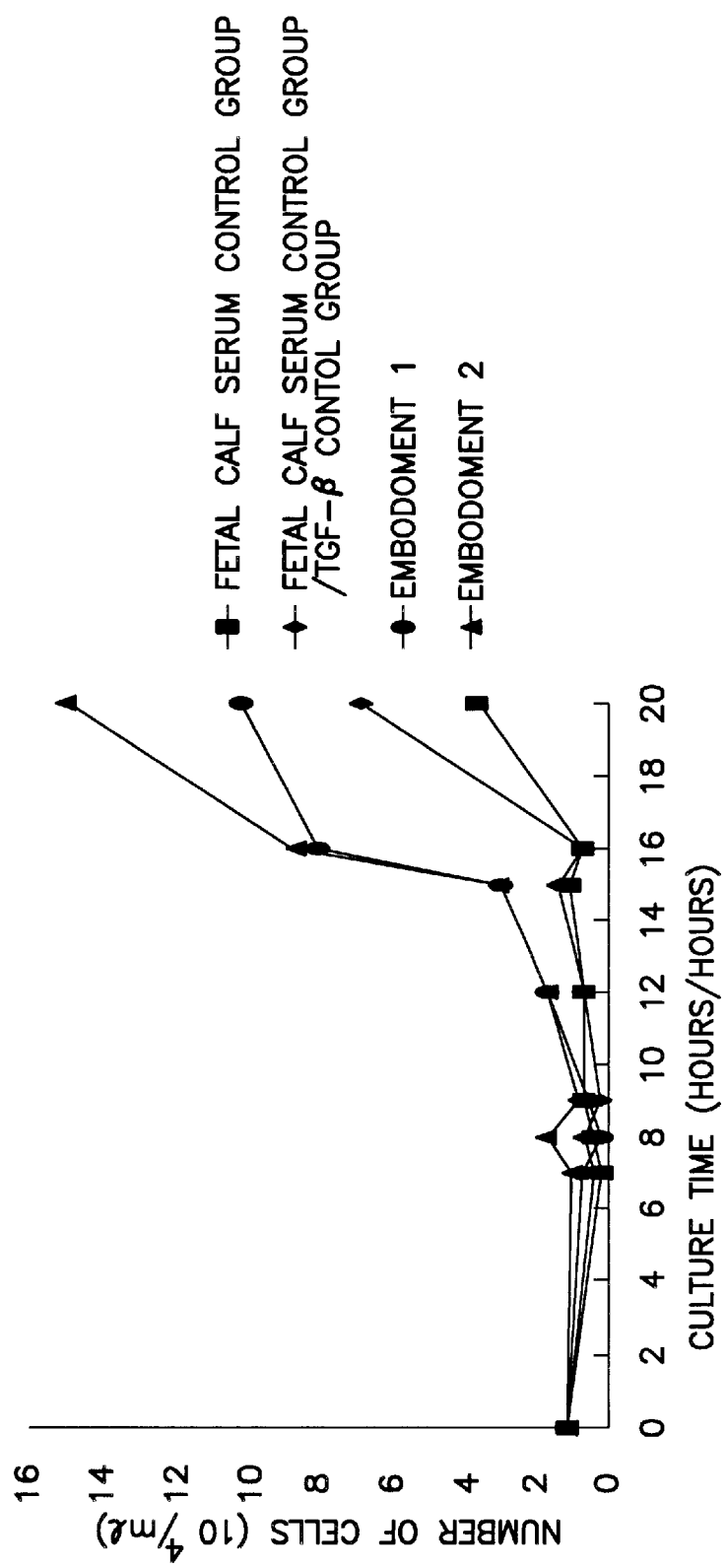
FIG. 1 is a graph to show proliferation of chondrocytes for 20 hours' cultivation.
Figure 2:
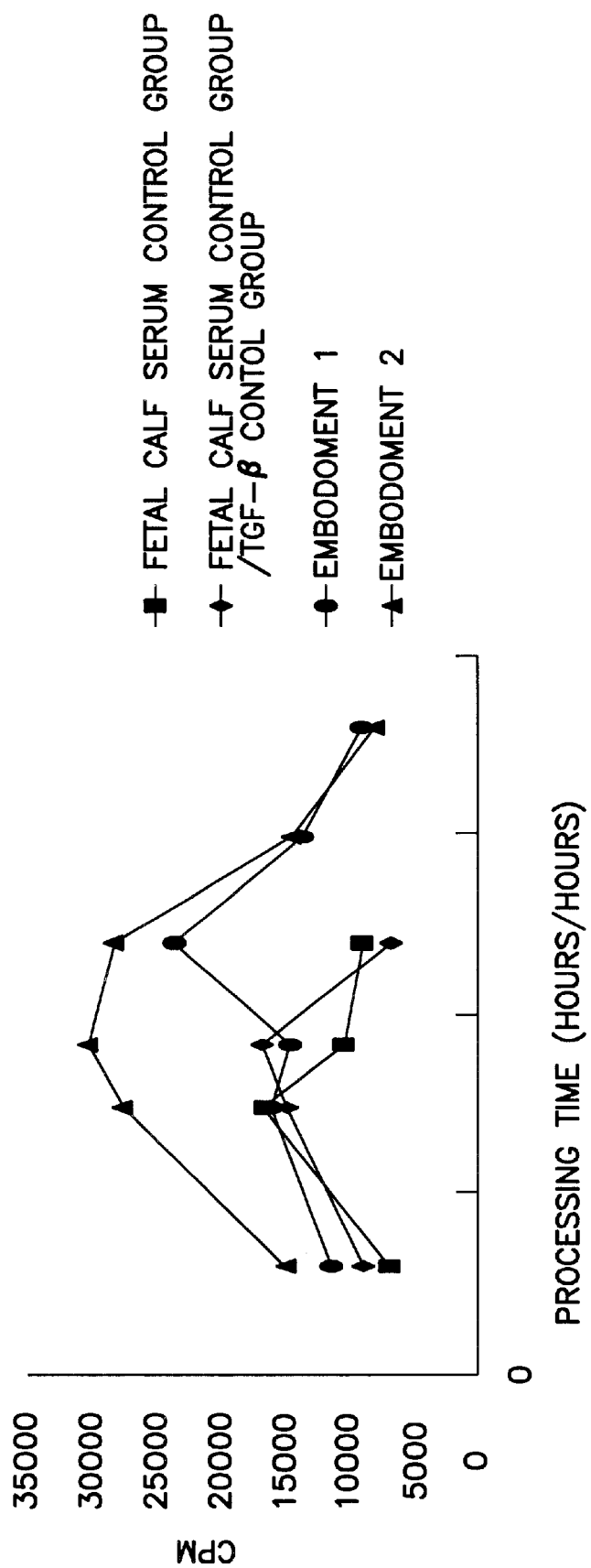
FIG. 2 is a graph to show a proliferation rate of chondrocytes for 80 hours' cultivation.

FIG. 1 is a graph to show proliferation of chondrocytes for 20 days' culture, and FIG. 2 is a graph to show a proliferation rate of chondrocytes for 80 days' culture. As shown in FIGS. 1 and 2, the proliferation rate of chondrocytes is the highest in the media solution cultured according to the second embodiment. Specifically in the media solution according to the second embodiment, the initial proliferation rate is very fast, which is considered that chondrocytes were easily adapted to the media comprising human serum. In this case, the proliferation period of chondrocytes was also extended The number of chondrocytes cultured according to the first and second embodiments was the most at the time 3 weeks after culturing started, and tended to decrease from the fourth week. Then the decrease rate of chondrocytes cultured according to the first and second embodiments was more insignificant than that in the case of the control groups and the common test group.

Accordingly, in this invention, the cells proliferation speed improved more effectively by using human serum than using fetal calf serum. By further using TGF-β, cell proliferation was more accelerated.

TEST EXAMPLE 2

Manifestation Rate of Second Type Collagen by Human Serum

To examine changes in the expression type by redifferentiation of chondrocytes, the amount of manifestation of the second type collagen was checked by performing Western Blot, using antibodies against the second type collagen (Chemicon International Inc.) with respect to the chondrocytes cultured according to the first and second embodiments.

Then, the amount of manifestation of the second type collagen was checked, using the media comprising fetal calf serum of 10% (fetal calf serum control group) and the media comprising fetal calf serum of 10% and 5 ng/ml TGF-β (fetal calf serum/TGF-β control group) were used as control groups.

Figure 3A:
FIGS. 3a and 3b are Western Blot results to show collagen manifestation in a first embodiment and at the step of cultivation of a fetal calf serum control group respectively.
Figure 3B:
Figure 3C:
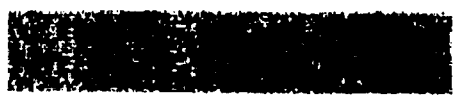
FIGS. 3c and 3d are Western Blot results to show collagen manifestation in a second embodiment and at the step of cultivation of a fetal calf serum/TGF-β control group respectively.
Figure 3D:

FIGS. 3a and 3b are the Western Blot results to show manifestation of the second type collagen at the time when 1, 2, 3, 4 and 5 week/weeks had passed after starting primary culture in the first embodiment and the fetal calf serum control group respectively, and at the time in three-dimensional culturing. FIGS. 3c and 3d are the Western blot results to show manifestation of second type collagen at the time when 1, 2, 3 and 4 week/weeks had passed after starting primary culture and in three-dimensional culturing, in the second embodiment and the fetal calf serum/TGF-β control group. As shown in FIGS. 3a and 3d, manifestation of the second type collagen ceased on the fifth week during the primary culturing step in the first and second embodiments embodiment and the control groups, and been resumed at the three-dimensional culturing step. Specifically in the media solution according to the second embodiment, manifestation of the second type collagen continued longer even at the primary culturing step, sad the amount of manifestation was remarkably increased than in the first embodiment and the control groups.

In this invention, therefore, the cell expression types may be more stably maintained and more effectively redifferentiated by using human serum, and such effects can be improved more effectively by using TGF-β.

In accordance with the media and the method of this invention, proliferation speed of human cells may increase and the culturing period may be shortened, by using human serum. The cells expression type may be also stably manifested. By further using TGF-β in the media and the media of this invention, such effects are improved more, effectively. Human cells obtained according to the method of this invention are not only useful for cell or tissue grafting, but there is no worry for any side effects.

What is claimed is:

1. Media for culturing human chondrocytes for transplantation, the media comprising human serum and a transforming growth factor (TGF-β).

2. The media of claim 1, wherein said human serum is from 1 to 50% (v/v).

3. The media of claim 1, wherein said human serum originates from AB-type blood.

4. The media of claim 1, further comprising at least one of insulin, transferrin, selenium and T3 hormone.

5. The media of claim 1, further comprising at least one of an insulin-like growth factor (IGF), a fibroblast growth factor (FGF), a platelet-derived growth factor (PDGF), a keratinocyte growth factor (KGF), and an epidermic growth factor (EGF).

6. The media of claim 1, wherein said human serum and said human chondrocytes originate from the same person.

* * * * *